United States Patent
Ohta et al.

(10) Patent No.: US 7,801,276 B2
(45) Date of Patent: Sep. 21, 2010

(54) RADIATION IMAGE CAPTURING SYSTEM AND METHOD OF CAPTURING RADIATION IMAGE

(75) Inventors: Yasunori Ohta, Yokohama (JP); Naoki Mochizuki, Minami-ashigara (JP); Daiki Harada, Minami-ashigara (JP); Hiroshi Fukuda, Minato-ku (JP); Eiichi Kito, Minami-ashigara (JP); Naoyuki Nishino, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/389,969

(22) Filed: Feb. 20, 2009

(65) Prior Publication Data

US 2009/0218528 A1 Sep. 3, 2009

(30) Foreign Application Priority Data

Feb. 29, 2008 (JP) .............................. 2008-051167
Feb. 13, 2009 (JP) .............................. 2009-031047

(51) Int. Cl.
*H05G 1/26* (2006.01)

(52) U.S. Cl. ...................................... 378/115; 378/205

(58) Field of Classification Search ......... 378/114–116, 378/102, 189, 196–197, 205, 206
See application file for complete search history.

(56) References Cited

U.S. PATENT DOCUMENTS

| 6,267,503 B1 | 7/2001 | McBride |
| 2004/0105526 A1* | 6/2004 | Zhang et al. ................. 378/205 |
| 2006/0285637 A1* | 12/2006 | Varjonen et al. .............. 378/62 |

FOREIGN PATENT DOCUMENTS

| JP | 2000-105297 A | 4/2000 |
| JP | 2001-504013 A | 3/2001 |
| JP | 2001-346796 A | 12/2001 |
| JP | 3494683 B2 | 11/2003 |

* cited by examiner

*Primary Examiner*—Hoon Song
(74) *Attorney, Agent, or Firm*—Sughrue Mion, PLLC

(57) ABSTRACT

A radiation image capturing system includes an image capturing apparatus for capturing a radiation image of a subject by a radiation emitted from a radiation source and applied through the subject, a detecting unit for detecting whether the radiation source is oriented to the image capturing apparatus or not, and a processor for setting an image capturing mode for the radiation image based on a detection result from the detecting unit and controlling a process of capturing the radiation image with the image capturing apparatus in the set image capturing mode.

6 Claims, 11 Drawing Sheets

RADIATION IMAGE CAPTURING SYSTEM AND METHOD OF CAPTURING RADIATION IMAGE

BACKGROUND OF THE INVENTION

1. Field of the Invention

The present invention relates to a radiation image capturing system and a method of capturing a radiation image of a subject by applying a radiation from a radiation source through the subject to an image capturing apparatus.

2. Description of the Related Art

In the medical field, there have widely been used radiation image capturing apparatus which apply a radiation to a subject and guide the radiation that has passed through the subject to a radiation conversion panel, which captures a radiation image from the radiation.

One known radiation conversion panel is a stimulable phosphor panel which stores a radiation energy representative of a radiation image in a phosphor. When the stimulable phosphor panel is irradiated with stimulating light, the phosphor emits stimulated light representative of the stored radiation image. The stimulable phosphor panel with the radiation image recorded therein is supplied to a reading apparatus which reads the stored radiation image as a visible radiation image.

In sites of medical practice such as operating rooms or the like, it is necessary to read recorded radiation image immediately from a radiation conversion panel for the purpose of quickly and appropriately treating the patient. As a radiation conversion panel which meets such a requirement, there has been developed a direct-conversion radiation conversion panel for directly converting a radiation into an electric signal or an indirect-conversion radiation conversion panel for converting a radiation into visible light with a scintillator and then converting the visible light into an electric signal to read a detected radiation image.

The radiation image capturing apparatus should desirably be capable of capturing a radiation image of a given body region of a patient accurately and reliably for thereby reducing burdens on the patient while the radiation image thereof is being captured.

According to the proposal disclosed in Japanese Laid-Open Patent Publication No. 2001-504013 (PCT), a reflective marker is applied to a patient at a give position thereon, and then light is applied from an infrared stroboscopic source to the patient. Light reflected from the reflective marker is detected by a camera device, and an X-ray apparatus (image capturing apparatus) is positioned with respect to the patient based on the light detected by the camera. Japanese Laid-Open Patent Publication No. 2001-346796 discloses a positioning adjuster wherein the head of a patient guided into an image capturing apparatus is imaged by a front camera and a side camera, various parts of the image capturing apparatus are automatically adjusted to accurate positions with respect to the head of the patient based on face image data of the patient from the cameras, and the patient is instructed to move the head.

According to the technologies disclosed in Japanese Laid-Open Patent Publication No. 2001-504013 (PCT) and Japanese Laid-Open Patent Publication No. 2001-346796, before a radiation image of the patient is captured, the position of the image capturing apparatus with respect to the patient is adjusted, or the position of the patient is moved into alignment with the image capturing apparatus, so that a radiation image of a given body region of the patient can accurately be obtained.

When the radiation image is captured, the radiation is applied from the radiation source through the patient (subject) to the image capturing apparatus including the radiation conversion panel. Therefore, before the radiation image is captured, it is necessary to determine whether the positional relationship between the image capturing apparatus and the subject is proper or not, and whether the positional relationship between the radiation source and the image capturing apparatus is proper or not, or more specifically, whether the radiation source is oriented toward the image capturing apparatus or not.

In other words, a processor for controlling the process of capturing the radiation image controls the image capturing apparatus based on an image capturing mode which is indicative of image capturing conditions for capturing the radiation image. If a plurality of image capturing apparatus are available for capturing a radiation image of a subject, then when one of the image capturing apparatus which is controlled by the processor to capture the radiation image based on the image capturing mode is different from another one of the image capturing apparatus toward which the radiation source is oriented, the radiation image of the subject cannot be obtained accurately and reliably.

SUMMARY OF THE INVENTION

It is an object of the present invention to capturing a radiation image of a subject accurately and reliably.

According to the present invention, there is provided a radiation image capturing system including an image capturing apparatus for capturing a radiation image of a subject by a radiation emitted from a radiation source and applied through the subject, a detecting unit for detecting whether the radiation source is oriented to the image capturing apparatus or not, and a processor for setting an image capturing mode for the radiation image based on a detection result from the detecting means and controlling a process of capturing the radiation image with the image capturing apparatus in the set image capturing mode.

According to the present invention, there is also provided a method of capturing a radiation image of a subject by applying a radiation from a radiation source through the subject to an image capturing apparatus, comprising a detecting step for detecting whether the radiation source is oriented to the image capturing apparatus or not, and a setting and controlling step for setting an image capturing mode for the radiation image based on a detection result from the detecting step and controlling a process of capturing the radiation image with the image capturing apparatus in the set image capturing mode.

Since it is determined whether the radiation source is oriented to the image capturing apparatus or not, and the image capturing mode is automatically set based on the detection result, the radiation image can be captured accurately and reliably, and also can be captured efficiently.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
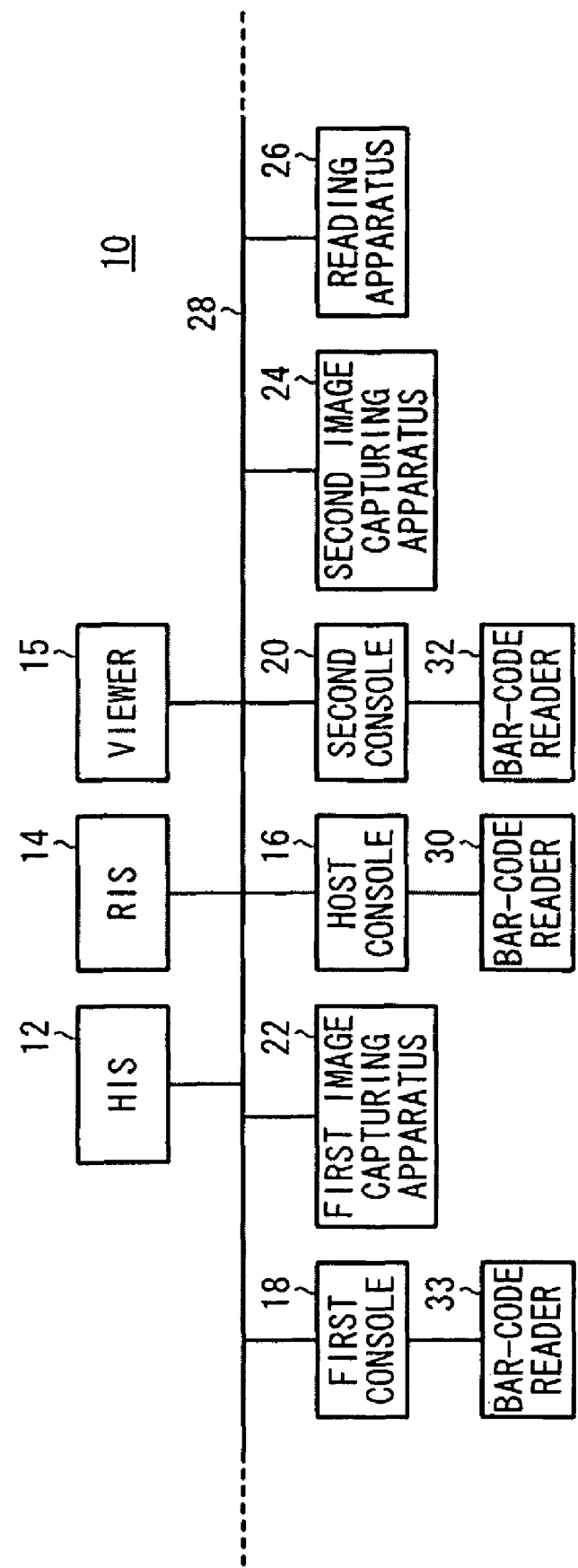
FIG. 1 is a block diagram of a radiation image capturing system according to an embodiment of the present invention.
Figure 2:
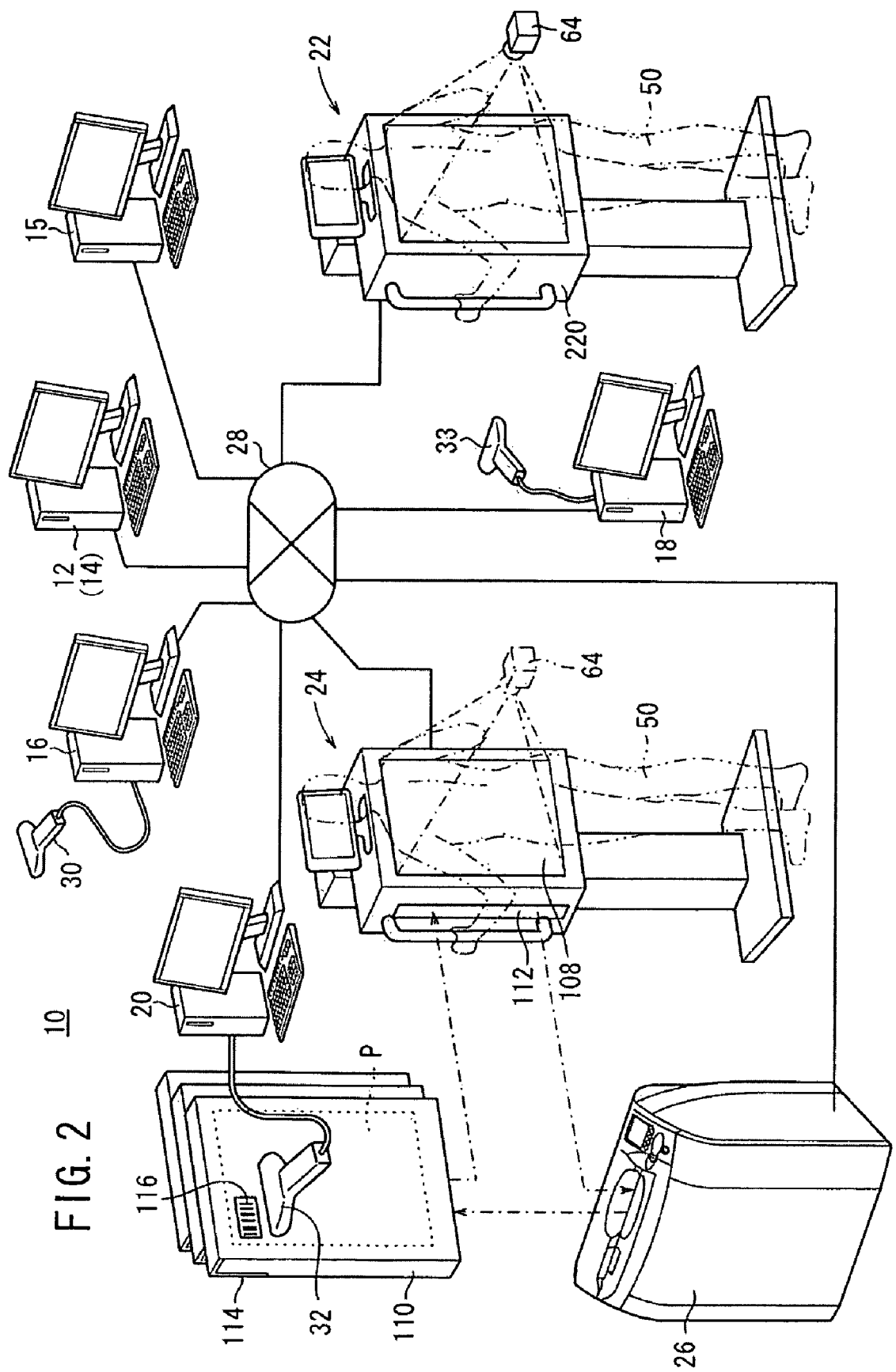
FIG. 2 is a schematic perspective view of the radiation image capturing system shown in FIG. 1.

FIGS. 1 and 2 show a configuration of a radiation image capturing system 10 according to an embodiment of the present invention. As shown in FIGS. 1 and 2, the radiation image capturing system 10 comprises a hospital information system (HIS) 12 for managing medical information in a hospital, a radiology information system (RIS) 14 for managing radiation image capturing processes performed in the radiological department of the hospital under the management of the HIS 12, a viewer 15 for displaying radiation images to be interpreted by the doctor for diagnosis, a host console (processor) 16 placed in a control room near image capturing rooms in the radiological department, for managing various image capturing apparatus, a first console (processor) 18 and a second console (processor) 20 placed in the control room for controlling particular image capturing apparatus, respectively, a first image capturing apparatus (one image capturing apparatus) 22 for being controlled by the first console 18, a second image capturing apparatus (another image capturing apparatus) 24 for being controlled by the second console 20, and a reading apparatus 26 for being controlled by the second console 20 for reading radiation image information captured by the second image capturing apparatus 24. The HIS 12, the RIS 14, the viewer 15, the host console 16, the first console 18, the second console 20, the first image capturing apparatus 22, the second image capturing apparatus 24, and the reading apparatus 26 are interconnected by an in-house network 28 in the hospital. If necessary, other consoles, other image capturing apparatus, and components may also be connected to the in-house network 28.

The host console 16 acquires patient information such as the name, gender, age, etc. of a patient which has been set using the HIS 12, and image capturing instruction information such as a method of capturing a radiation image, a body region to be imaged, and an image capturing apparatus to be used to capture a radiation image, which has been set by the doctor or radiological technician using the RIS 14, through the in-house network 28, and supplies the acquired information to the first console 18 or the second console 20. The host console 16 may be programmed to perform the processing sequence of the first console 18 or the second console 20.

If the host console 16 is programmed to perform the processing sequence of the first console 18 or the second console 20, then since the first console 18 or the second console 20 may be dispensed with, the radiation image capturing system will become less costly. To the host console 16, there is connected a bar-code reader 30 for acquiring ID information for identifying a radiation conversion panel, described later, to be used in the second image capturing apparatus 24. A bar-code reader 33 for acquiring the ID information is connected to the first console 18. A bar-code reader 32 for acquiring the ID information is connected to the second console 20.

Figure 3:
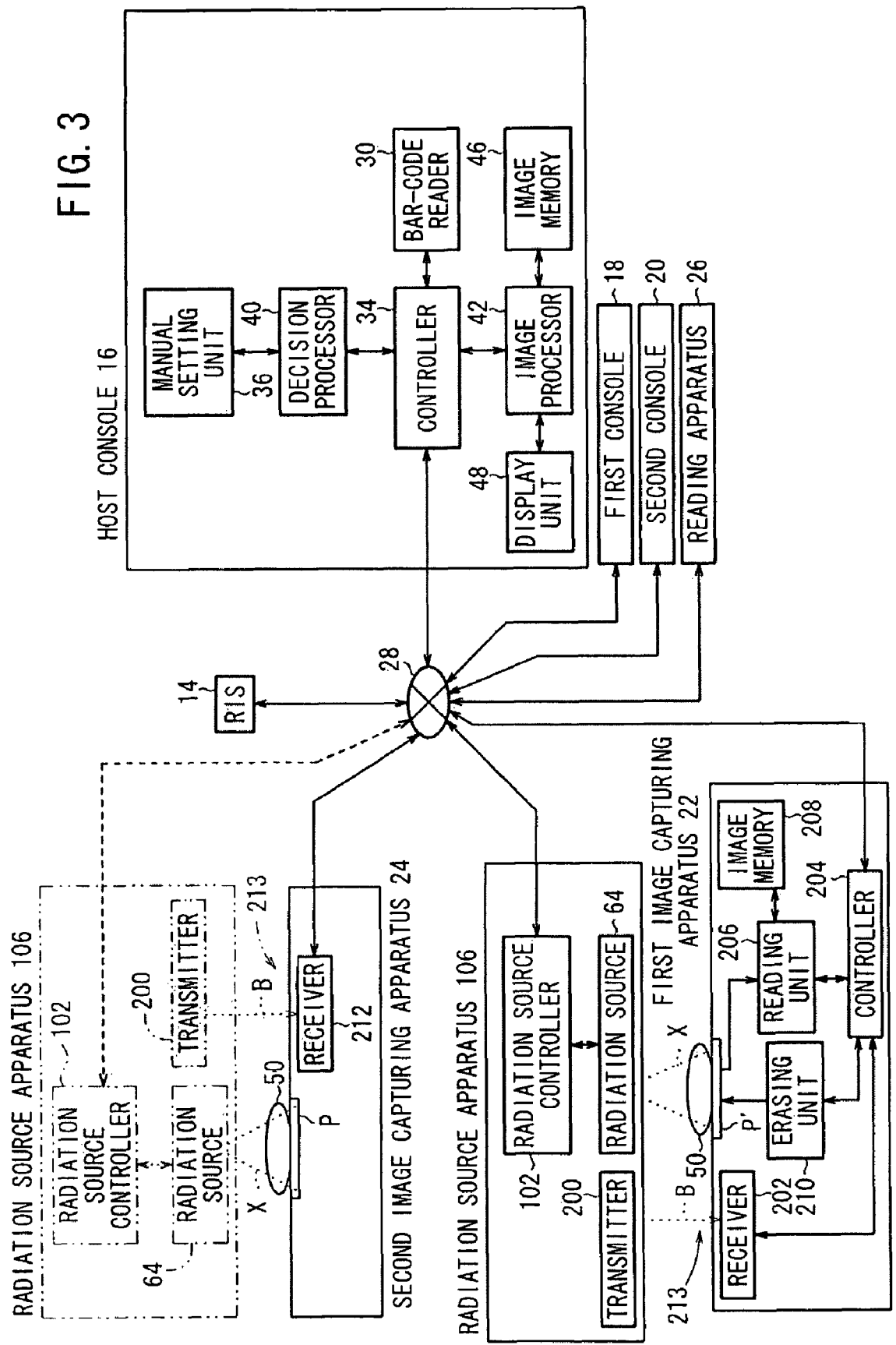
FIG. 3 is a block diagram of an assembly of a host console, a first image capturing apparatus, a second image capturing apparatus, and a radiation source apparatus of the radiation image capturing system.

FIG. 3 shows in block form an assembly of the host console 16, the first image capturing apparatus 22, the second image capturing apparatus 24, and a radiation source apparatus 106.

The host console 16 has a controller 34 which sends information to and receives information from the RIS 14, the first console 18, the second console 20, the first image capturing apparatus 22, the second image capturing apparatus 24, the reading apparatus 26, and the radiation source apparatus 106.

The host console 16 comprises a manual setting unit 36, a decision processor (decision means) 40 for regarding patient information and image capturing instruction information set through the manual setting unit 36, or patient information and image capturing instruction information set through the RIS 14, as an image capturing mode for capturing a radiation image, and performing a predetermining decision process, the controller 34 for directly controlling the first image capturing apparatus 22 or the second image capturing apparatus 24 which corresponds to a set image capturing mode to capture a radiation image, or supplying an image capturing mode to the first console 18 or the second console 20, an image processor 42 for processing radiation image information acquired from the first image capturing apparatus 22 or the second image capturing apparatus 24, an image memory 46 for storing the processed radiation image information, and a display unit 48 for displaying the radiation image information.

When the controller 34 supplies an image capturing mode to the first console 18 or the second console 20, the first console 18 or the second console 20 which is supplied with the image capturing mode controls the first image capturing apparatus 22 or the second image capturing apparatus 24 based on the image capturing mode which corresponds to the first image capturing apparatus 22 or the second image capturing apparatus 24.

The image capturing mode represents patient information and image capturing instruction information representative of image capturing conditions for capturing a radiation image of a subject 50 by applying a radiation X from a radiation source 64 of the radiation source apparatus 106 through the subject 50 to the first image capturing apparatus 22 or the second image capturing apparatus 24. The radiation image capturing system 10 has different image capturing modes for the respective first and second image capturing apparatus 22, 24.

In FIGS. 1 through 3, since the radiation image capturing system 10 includes the first and second image capturing apparatus 22, 24, the host console 16, the first console 18, and the second console 20 have an image capturing mode (first mode) for the first image capturing apparatus 22 and an image capturing mode (second mode) for the second image capturing apparatus 24. For capturing a radiation image, either one of the first and second modes is selected, and the image capturing apparatus corresponding to the selected mode is controlled. For example, if the first mode is selected, then the first image capturing apparatus 22 is controlled, and if the second mode is selected, then the second image capturing apparatus 24 is controlled.

The first console 18 and the second console 20 have substantially the same functions as the host console 16. In FIG. 3, the internal details of the first console 18 and the second console 20 are omitted from illustration.

Figure 4:
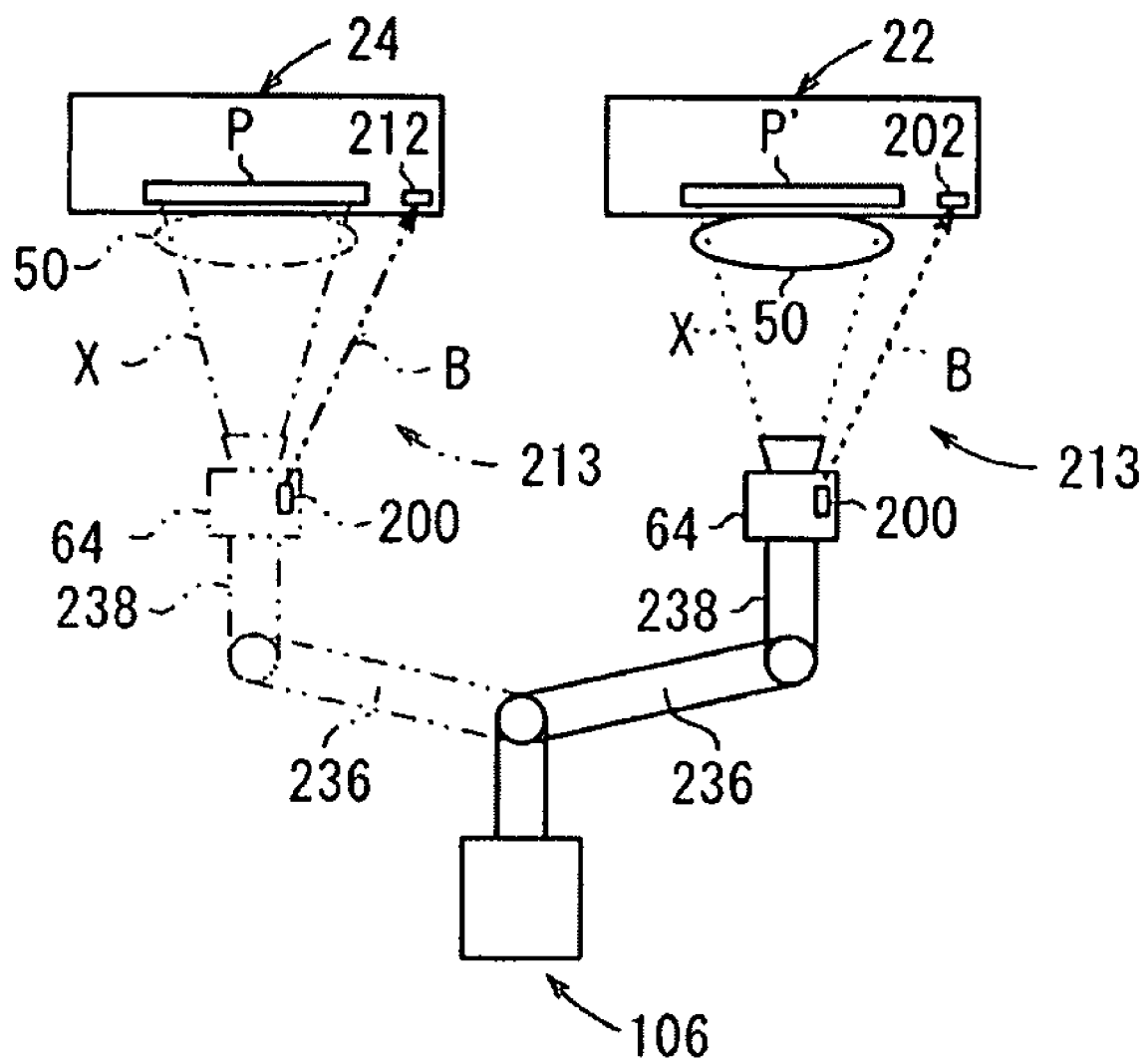
FIG. 4 is a schematic view showing the positional relationship between a radiation source and image capturing apparatus.

As shown in FIGS. 2 through 4, the radiation source apparatus 106 comprises a radiation source controller 102 and the radiation source 64 which is controlled by the radiation source controller 102. The radiation source 64 can be brought into a position facing the first image capturing apparatus 22 or the second image capturing apparatus 24 when the radiological technician manually moves arms 236, 238 (see FIG. 4).

The radiation source apparatus 106 includes a transmitter 200, and the first image capturing apparatus 22 and the second image capturing apparatus 24 have respective receivers 202, 212. The transmitter 200 and the receivers 202, 212 jointly make up contactless detecting means (detecting unit) 213 such as optical, ultrasonic, or wireless detecting means. When the radiation source 64 is brought into the position facing the first image capturing apparatus 22 or the second image capturing apparatus 24 by the radiological technician who moves the arms 236, 238, a signal B (an optical signal, an ultrasonic signal, or a wireless signal) emitted from the transmitter 200 is received by the receiver 202 of the first image capturing apparatus 22 or the receiver 212 of the second image capturing apparatus 24. The received signal B is output as a detected signal from the receiver 202 or the receiver 212 through the in-house network 28 to the controller 34.

Based on the detected signal B, the decision processor 40 determines which of the first image capturing apparatus 22 and the second image capturing apparatus 24 the radiation source 64 faces or is oriented to. Based on the determined result, the decision processor 40 selects one of the image capturing modes which the console has, and sets the selected image capturing mode as the image capturing mode for the console.

Specifically, the decision processor 40 of the host console 16 identifies which of the receiver 202 and the receiver 212 has emitted the signal B, selects one of the image capturing modes which the host console 16 has, depending on the image capturing apparatus that has the identified receiver, and sets the selected image capturing mode as the image capturing mode for the image capturing apparatus to capture a radiation image of the subject 50.

The decision processor 40 of the first console 18 or the second console 20 determines which of the receiver 202 and the receiver 212 has output the signal B. If the signal B has been output from the receiver of the image capturing apparatus that is controlled by the console thereof, then the decision processor 40 selects the image capturing mode for the image capturing apparatus from all the image capturing modes which the first console 18 or the second console 20 has, and sets the selected image capturing mode as the image capturing mode for capturing a radiation image with the image capturing apparatus. Specifically, if the signal B has been output from the receiver 202, then the decision processor 40 of the first console 18 sets the first mode for the first image capturing apparatus 22 as the image capturing mode therefore, and if the signal B has been output from the receiver 212, then the decision processor 40 of the second console 20 sets the second mode for the second image capturing apparatus 24 as the image capturing mode therefore.

Each of the first image capturing apparatus 22 and the second image capturing apparatus 24 is an upstanding image capturing apparatus for capturing a radiation image of the chest or the like of the subject 50. However, the first image capturing apparatus 22 and the second image capturing apparatus 24 have different internal structural details.

As shown in FIGS. 2 through 5, the first image capturing apparatus 22 comprises an image capturing base 220 for positioning a body region of the subject 50 to be imaged, and a casing 222 housing the image capturing base 220 and other members, to be described below, of the first image capturing apparatus 22 therein in a light-shielded fashion. The first image capturing apparatus 22 is controlled by the first console 18 or the host console 16 through the in-house network 28.

The casing 222 has therein a stimulable phosphor panel P' built-in substantially parallel to the image capturing base 220, a reading unit 206 for reading a radiation image recorded in the stimulable phosphor panel P', and an erasing unit 210 for erasing a remaining radiation image from the stimulable phosphor panel P' after the desired radiation image has been read therefrom.

Figure 5:
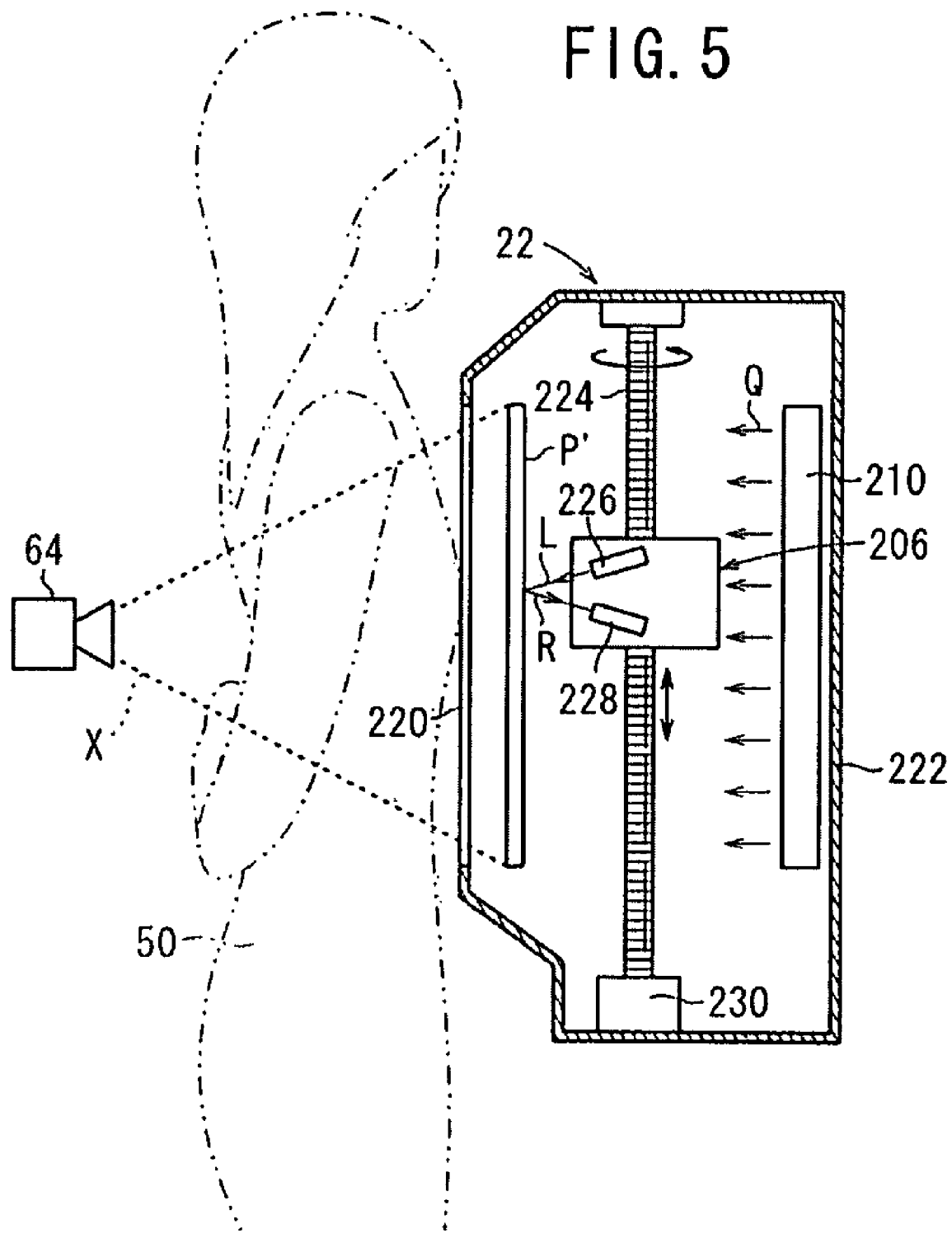
FIG. 5 is a cross-sectional view showing internal structural details of the first image capturing apparatus.

The stimulable phosphor panel P' housed in the casing 222 may be a hard panel comprising a support body of a hard material such as glass or the like and a stimulable phosphor layer disposed on the support body for storing the energy of the radiation X emitted from the radiation source 64. Alternatively, the stimulable phosphor panel P' may be in the form of a flexible sheet comprising a flexible support body coated with a stimulable phosphor layer. In FIG. 5, the stimulable phosphor panel P' comprises a transparent support substrate and a stimulable phosphor layer disposed thereon. The stimulable phosphor panel P' records a radiation image based on a radiation applied to one surface thereof. The recorded radiation image is read from the other surface of the stimulable phosphor panel P', and a remaining radiation image is also erased from the other surface of the stimulable phosphor panel P'. However, the stimulable phosphor panel P' may be constructed such that a radiation image can be recorded in, the recorded radiation image can be read from, and a remaining radiation image can be erased from, one surface of the stimulable phosphor panel P'.

The reading unit 206 is operatively threaded over a ball screw 224 extending vertically in the casing 222. When the ball screw 224 is rotated about its own axis in the direction indicated by the arrow by a drive motor 230 coupled to the lower end of the ball screw 224, the reading unit 206 is vertically moved along the ball screw 224 and the stimulable phosphor panel P'. The reading unit 206 comprises a stimulating light source 226 for applying stimulating light L to the stimulable phosphor panel P' with a radiation image recorded therein, and a photoelectric transducer 228 for detecting stimulated light R representative of the recorded radiation image which is emitted from the stimulable phosphor panel P' when it is irradiated with the stimulating light L and converting the detected stimulated light R into an electric signal.

The stimulating light source 226 may comprise a linear array of laser diodes disposed along a main scanning direction. The photoelectric transducer 228 may comprise a CCD line sensor for detecting the stimulated light R that is emitted from the stimulable phosphor panel P' when it is irradiated with the stimulating light L from the stimulating light source 226 as it scans the stimulable phosphor panel P' in the main scanning direction. When the reading unit 206 is moved on the rotating ball screw 224 along the stimulable phosphor panel P' in auxiliary scanning directions indicated by the arrows which are perpendicular to the main scanning direction, the reading unit 206 two-dimensionally reads the radiation image recorded in the stimulable phosphor panel P'.

The second image capturing apparatus 24 comprises an image capturing base 108 having a slot 112, defined in a side wall thereof, through which a cassette 110 housing a stimulable phosphor panel P therein can be loaded into the image capturing base 108. The second image capturing apparatus 24 is controlled by the second console 20 or the host console 16 through the in-house network 28.

The stimulable phosphor panel P housed in the cassette 110 comprises a support body and a stimulable phosphor layer disposed on the support body. The stimulable phosphor layer stores the energy of the radiation X that is applied thereto. When the stimulable phosphor layer is irradiated with stimulating light, it emits stimulated light depending on the stored energy. When the stimulable phosphor layer is irradiated with erasing light, it discharges any remaining energy stored therein and can be reused.

The stimulable phosphor panel P housed in the cassette 110 is removable from the cassette 110 when a lid member 114 on the cassette 110 is opened. A bar code 116 which records therein identification information including an identification number for identifying the stimulable phosphor panel P housed in the cassette 110, the size of the stimulable phosphor panel P, the sensitivity of the stimulable phosphor panel P, etc. is attached to an outer surface of the cassette 110. The bar code 116 can be read by each of the bar-code readers 30, 32, 33.

Figure 6:
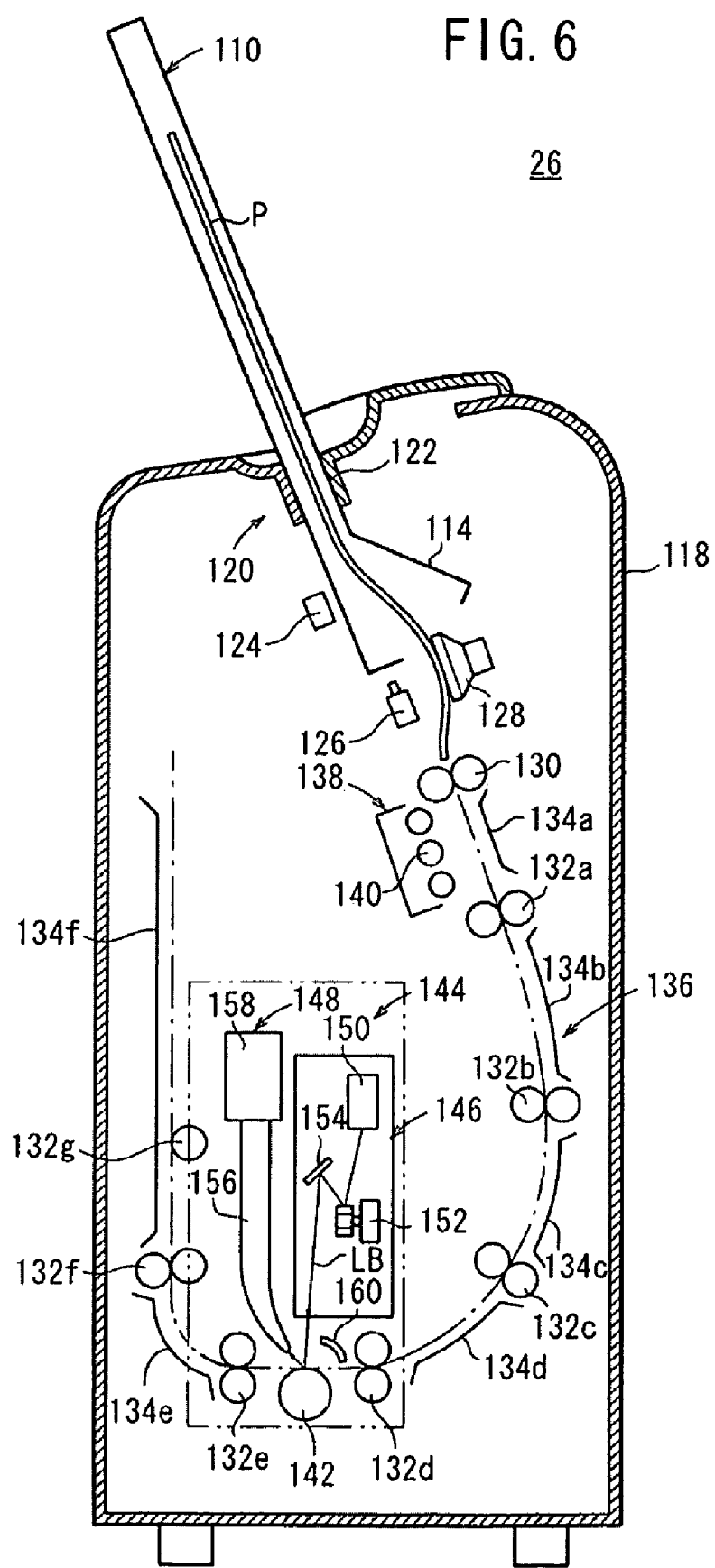
FIG. 6 is a cross-sectional view of a reading apparatus of the radiation image capturing system.

Radiation image information that is recorded in the stimulable phosphor panel P is read by the reading apparatus 26 which is constructed as shown in FIG. 6. The reading apparatus 26 and the second image capturing apparatus 24 are controlled by the second console 20 through the in-house network 28.

As shown in FIG. 6, the reading apparatus 26 has a cassette loader 120 disposed in an upper portion of a casing 118 and having a loading slot 122 for receiving therein the cassette 110 which houses therein the stimulable phosphor panel P with recorded radiation image information. The casing 118 of the reading apparatus 26 accommodates therein, near the loading slot 122, a bar-code reader 124 for reading the identification information recorded in the bar code 116 on the cassette 110, an unlock mechanism 126 for unlocking the lid member 114 of the cassette 110, a suction cup 128 for attracting and removing the stimulable phosphor panel P from the cassette 110 at the time the lid member 114 is opened, and a pair of nip rollers 130 for gripping and feeding the stimulable phosphor panel P removed by the suction cup 128.

The nip rollers 130 are followed by a plurality of feed rollers 132a through 132g and a plurality of guide plates 134a through 134f which jointly make up a curved feed path 136. The curved feed path 136 extends downwardly from the cassette loader 120, then extends substantially horizontally at its lowermost portion, and then extends substantially vertically upwardly. The curved feed path 136 thus shaped is effective to make the reading apparatus 26 small in size.

Between the nip rollers 130 and the feed rollers 132a, there is disposed an erasing unit 138 for erasing radiation image information remaining in the stimulable phosphor panel P from which radiation image information has been read. The erasing unit 138 has a plurality of erasing light sources 140 such as cold cathode tubes or the like for emitting erasing light.

A platen roller 142 is disposed between the feed rollers 132d, 132e which are positioned in the lowermost portion of the curved feed path 136. The platen roller 142 is disposed beneath a scanning unit 144 for reading the desired radiation image information recorded in the stimulable phosphor panel P.

The scanning unit 144 comprises a stimulator 146 for emitting a laser beam LB as stimulating light to scan the stimulable phosphor panel P and a reader 148 for reading stimulated light emitted from the stimulable phosphor panel P which is stimulated by the laser beam LB, the stimulated light being representative of the radiation image information.

The stimulator 146 comprises a laser oscillator 150 for outputting the laser beam LB, a rotary polygon mirror 152 for deflecting the laser beam LB in a main scanning direction across the stimulable phosphor panel P, and a reflecting mirror 154 for reflecting the laser beam LB to the stimulable phosphor panel P as it passes over the platen roller 142.

The reader 148 comprises a light guide 156 having a lower end disposed near the stimulable phosphor panel P over the platen roller 142, and a photomultiplier 158 connected to an upper end of the light guide 156 for converting the stimulated light from the stimulable phosphor panel P into an electric signal which represents the radiation image information stored in the stimulable phosphor panel P. A light collecting mirror 160 for collecting the stimulated light from the stimulable phosphor panel P is disposed near the lower end of the light guide 156. The photomultiplier 158 supplies the electric signal representing the radiation image information to the second console 20 through the in-house network 28.

Another image capturing apparatus which employs the cassette 110 which is loadable with the stimulable phosphor panel P therein as shown in FIG. 2, and/or another image capturing apparatus which houses therein the built-in type stimulable phosphor panel P' may be connected to the in-house network 28. In addition, a recumbent image capturing apparatus and a mammographic apparatus which employ the stimulable phosphor panels P, P' may also be connected to the in-house network 28. Furthermore, image capturing apparatus of other specifications, such as a CT apparatus, an MR apparatus, etc. may also be connected to the in-house network 28, and consoles (processors) for controlling these image capturing apparatus may also be connected to the in-house network 28.

The radiation image capturing system 10 according to the present invention is basically constructed as described above. Operation of the radiation image capturing system 10 will be described below with reference to FIGS. 1 through 7.

First, patient information such as the name, gender, age, etc. of a patient is set using the HIS 12, and image capturing instruction information such as a method of capturing a radiation image, a body region to be imaged, and an image capturing apparatus to be used to capture a radiation image, is set in relation to the patient information using the RIS 14.

The controller 34 of the host console 16 that is installed in the radiological department acquires the patient information and the image capturing instruction information from the RIS 14 via the in-house network 28. The radiological technician sets and changes the image capturing instruction information using the manual setting unit 36 of the host console 16. For example, the radiological technician changes the image capturing apparatus set by the doctor using the RIS 14 to an image capturing apparatus which corresponds to the body region to be imaged and the state of the patient. The patient information and the image capturing instruction information which has been acquired or the image capturing instruction information which has been changed or newly set is stored in a memory, not shown.

Then, the controller 34 of the host console 16 reads the patient information and the image capturing instruction information (image capturing mode) from the memory, and outputs the read image capturing mode to the first console 18 and the second console 20 via the in-house network 28.

Figure 7:
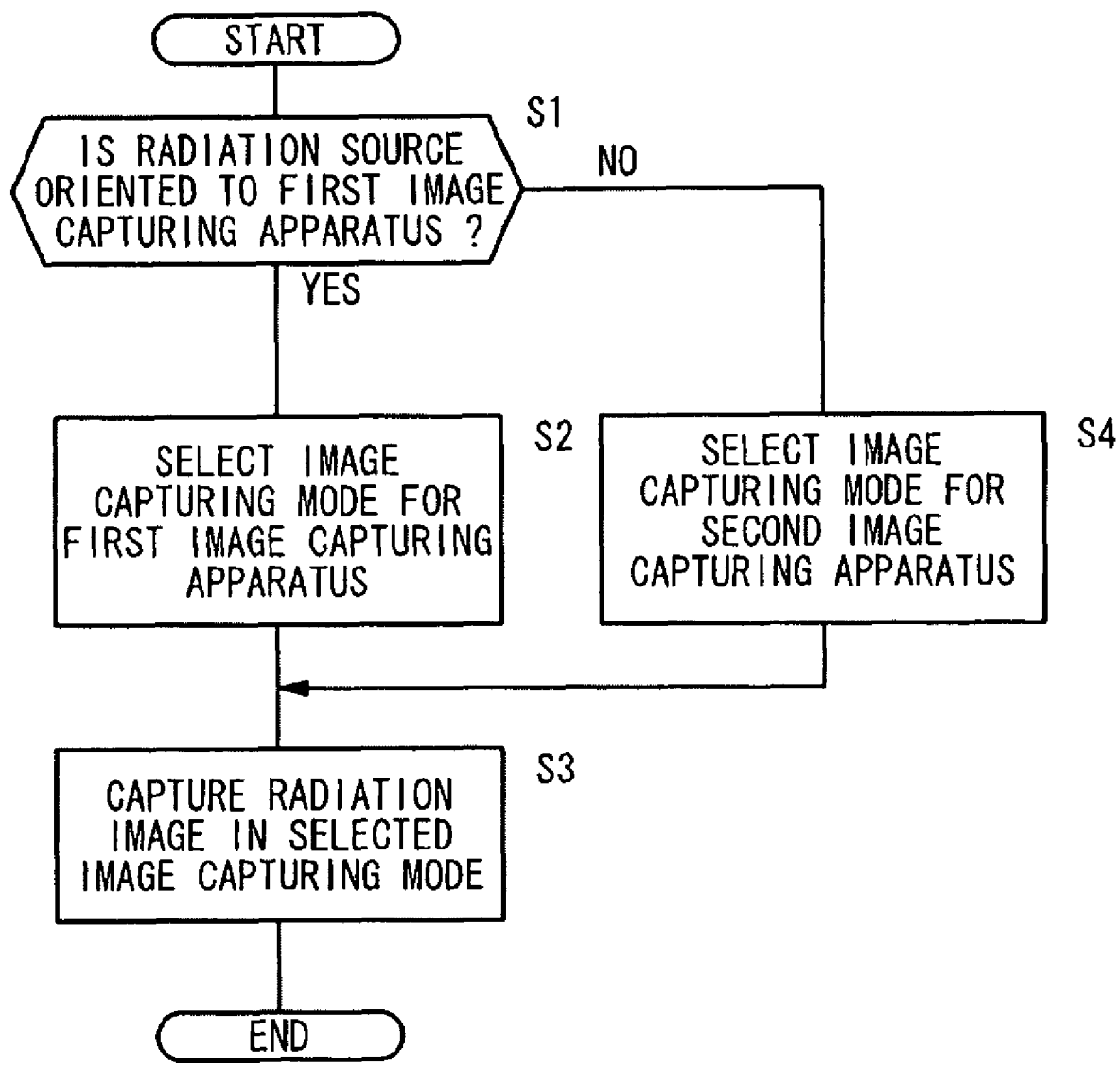
FIG. 7 is a flowchart of a processing sequence of a decision processor and a controller.

FIG. 7 is a flowchart of a processing sequence of the controller 34 and the decision processor 40 which is carried out before the first image capturing apparatus 22 or the second image capturing apparatus 24 captures a radiation image of the patient.

The processing sequence of the controller 34 and the decision processor 40 in the host console 16 will be described below.

First, the decision processor 40 in the host console 16 determines which of the first image capturing apparatus 22 and the second image capturing apparatus 24 has output the signal B that is supplied to the host console 16 (step S1). If the signal B is supplied from the receiver 202 (YES in step S1), then the decision processor 40 recognizes that the radiation source 64 and the first image capturing apparatus 22 are facing each other, and radiation image information of the subject 50 can be obtained accurately and reliably when the radiation source 64 applies the radiation X to the first image capturing apparatus 22. The decision processor 40 selects the first mode for the first image capturing apparatus 22 from all the image capturing modes which the host console 16 has (step S2). The controller 34 then permits the first image capturing apparatus 22 to capture a radiation image of the subject 50 in the first mode (step S3).

If the signal B is supplied from the receiver 212 (NO in step S1), then the decision processor 40 recognizes that the radiation source 64 and the second image capturing apparatus 24 are facing each other, and radiation image information of the subject 50 can be obtained accurately and reliably when the radiation source 64 applies the radiation X to the second image capturing apparatus 24. The decision processor 40 selects the second mode for the second image capturing apparatus 24 from all the image capturing modes which the host console 16 has (step S4). The controller 34 then permits the second image capturing apparatus 24 to capture a radiation image of the subject 50 in the second mode (step S3).

If the decision processor 40 of the first console 18 is to perform the above processing sequence, then the decision processor 40 determines whether the signal B is supplied from the receiver 202 or not (step S1). If the signal B is supplied from the receiver 202 (YES in step S1), then the decision processor 40 selects the first mode for the first image capturing apparatus 22 from all the image capturing modes which the first console 18 has (step S2).

If the decision processor 40 of the second console 20 is to perform the above processing sequence, then the decision processor 40 determines whether the signal B is supplied from the receiver 212 or not (step S1). If the signal B is supplied from the receiver 212 (NO in step S1), then the decision processor 40 selects the second mode for the second image capturing apparatus 24 from all the image capturing modes which the second console 20 has (step S4).

Thereafter, an image capturing process, to be described below, is performed (step S3).

An image capturing sequence in which the first console 18 controls the first image capturing apparatus 22, and an image capturing sequence in which the second console 20 controls the second image capturing apparatus 24 will be described below.

First, the image capturing sequence in which the first console 18 controls the first image capturing apparatus 22 to capture a radiation image of the chest of the subject 50 will be described below.

The first console 18 sets the image capturing conditions such as a tube voltage, a tube current, and an irradiation time included in the image capturing instruction information of the first mode, in the radiation source controller 102 of the radiation source apparatus 106 which is facing the first image capturing apparatus 22.

Then, the radiological technician presses an exposure switch, not shown, to start capturing a radiation image. According to the set image capturing conditions, the radiation source controller 102 controls the radiation source 64 to apply a radiation X to the subject 50. The radiation X that has passed through the subject 50 is applied to the stimulable phosphor panel P' housed in the casing 222 of the first image capturing apparatus 22. As a result, radiation image information of the subject 50 is recorded in the stimulable phosphor panel P'.

Thereafter, the reading unit 206 is energized by the controller 204 to start a reading process. When the drive motor 230 is energized, the ball screw 224 rotates about its own axis, moving the reading unit 206 in the auxiliary scanning directions indicated by the arrows in FIG. 5 along the stimulable phosphor panel P'. At this time, a line of the stimulating light L emitted from the stimulating light source 226 is applied to the stimulable phosphor panel P' while it is scanning the stimulable phosphor panel P' in the main scanning direction. Upon exposure to the stimulating light L, the stimulable phosphor panel P' emits stimulated light R representative of the recorded radiation image information. The emitted stimulated light R is converted by the photoelectric transducer 228 into an electric signal which is representative of the recorded radiation image information. The electric signal, i.e., the radiation image information, is then stored in the image memory 208. The radiation image information recorded in the stimulable phosphor panel P' is two-dimensionally read therefrom by the reading unit 206.

After the recorded radiation image information is read from the stimulable phosphor panel P' by the reading unit 206, the erasing unit 210 is energized to erase any remaining radiation image from the stimulable phosphor panel P'.

The radiation image information stored in the image memory 208 is sent from the controller 204 to the first console 18 via the in-house network 28. The first console 18 processes the received radiation image information and, if necessary, displays a radiation image based on the processed radiation image information for the radiological technician to confirm the radiation image. Thereafter, the first console 18 transmits the radiation image information to the viewer 15 through the in-house network 28. The doctor then interprets for diagnosis a radiation image that is displayed by the viewer 15 based on the radiation image information.

The image capturing sequence in which the second console 20 controls the second image capturing apparatus 24 to capture a radiation image of the chest of the subject 50 will be described below.

The second console 20 sets the image capturing conditions such as a tube voltage, a tube current, and an irradiation time included in the image capturing instruction information of the second mode, in the radiation source controller 102 of the radiation source apparatus 106 which is facing the second image capturing apparatus 24.

The radiological technician uses the bar-code reader 32 connected to the second console 20 to read the bar code 116 attached to the cassette 110, thereby acquiring identification information including an identification number for identifying the stimulable phosphor panel P housed in the cassette 110, the size of the stimulable phosphor panel P, the sensitivity of the stimulable phosphor panel P, etc.

After having loaded the cassette 110 into the slot 112 of the second image capturing apparatus 24, the radiological technician operates an exposure switch, not shown, to start an image capturing process. The radiation source controller 102 controls the radiation source 64 according to the set image capturing conditions to apply a radiation X to the subject 50. The radiation X that has passed through the subject 50 is applied to the stimulable phosphor panel P housed in the cassette 110. As a result, radiation image information of the subject 50 is recorded in the stimulable phosphor panel P.

The radiological technician then removes the cassette 110 housing therein the stimulable phosphor panel P with the recorded radiation image information from the second image capturing apparatus 24, and thereafter loads the cassette 110 into the cassette loader 120 of the reading apparatus 26.

When the cassette 110 is loaded into the cassette loader 120, the bar-code reader 124 in the cassette loader 120 reads the bar code 116 attached to the cassette 110 to acquire the identification information including the identification number, the size, the sensitivity, etc. of the stimulable phosphor panel P. The acquired identification information is compared with the identification information read by the bar-code reader 32 connected to the second console 20 to confirm the correspondence between the subject 50 and the radiation image information.

After the identification information is read, the unlock mechanism 126 is actuated to unlock and open the lid member 114. The suction cup 128 attracts the stimulable phosphor panel P, removes the stimulable phosphor panel P out of the cassette 110, and feeds the stimulable phosphor panel P between the nip rollers 130. The stimulable phosphor panel P which is gripped by the nip rollers 130 is then fed through the curved feed path 136 made up of the feed rollers 132*a* through 132*g* and the guide plates 134*a* through 134*f* to a position beneath the scanning unit 144.

Beneath the scanning unit 144, the stimulable phosphor panel P is fed substantially horizontally in an auxiliary scanning direction by the feed rollers 132*d*, 132*e*. At the same time, the laser beam LB output from the laser oscillator 150 of the stimulator 146 is reflected and deflected by the polygon mirror 152 that is rotating at a high speed, and then guided by the reflecting mirror 154 to the stimulable phosphor panel P whose lower surface is supported by the platen roller 142, thereby scanning the stimulable phosphor panel P in a main scanning direction.

By being irradiated with the laser beam LB, the stimulable phosphor panel P is stimulated to emit stimulated light representative of the radiation image information recorded therein. The stimulated light is applied directly or via the light collecting mirror 160 to the lower end of the light guide 156 which is disposed near the stimulable phosphor panel P and extends in the main scanning direction. The stimulated light which has entered the light guide 156 is repeatedly reflected in the light guide 156 and guided to the photomultiplier 158. The photomultiplier 158 converts the stimulated light into an electric signal representative of the radiation image information recorded in the stimulable phosphor panel P. In this manner, the radiation image information recorded in the stimulable phosphor panel P is read by the scanning unit 144 of the reading apparatus 26.

The radiation image information thus read by the scanning unit 144 is transmitted to the second console 20 through the in-house network 28. The second console 20 processes the received radiation image information and, if necessary, displays a radiation image based on the processed radiation image information for the radiological technician to confirm the radiation image, and then transmits the radiation image information to the viewer 15 through the in-house network 28. The doctor then interprets for diagnosis a radiation image that is displayed by the viewer 15 based on the radiation image information.

As described above, the radiation image capturing system 10 and the method of capturing a radiation image carried out thereby according to the present embodiment detect whether the radiation source 64 is oriented to an image capturing apparatus or not, and automatically set an image capturing mode based on the detection result. Accordingly, a radiation image can be captured accurately and reliably, and also can be captured efficiently.

If the radiation source 64 is detected as being oriented to an image capturing apparatus, then the console controls the image capturing apparatus to capture a radiation image based on the image capturing mode therefore. The image capturing apparatus can thus capture the radiation image efficiently.

If there are a plurality of image capturing apparatus and the console has a plurality of image capturing modes for the respective image capturing apparatus, then the console selects one of the image capturing modes for the image capturing apparatus to which the radiation source 64 is oriented, based on the detection result. Based on the selected image capturing mode, the console controls the image capturing apparatus to which the radiation source 64 is oriented in order to capture a radiation image. Since the console automatically sets one of the image capturing modes, burden on the radiological technician in the process of capturing the radiation image is reduced.

The radiation source 64 has the transmitter 200 and the image capturing apparatus 22, 24 have the receivers 202, 212. Either one of the receivers 202, 212 detects the signal B emitted from the transmitter 200, and outputs the detected signal B as the detection result to the console. In this manner, it is possible to detect whether the radiation source 64 is oriented to an image capturing apparatus or not, with a simple arrangement.

The present invention is not limited to the above embodiment, but many changes and modifications may be made to the illustrated embodiment within the scope of the invention.

Figure 8:
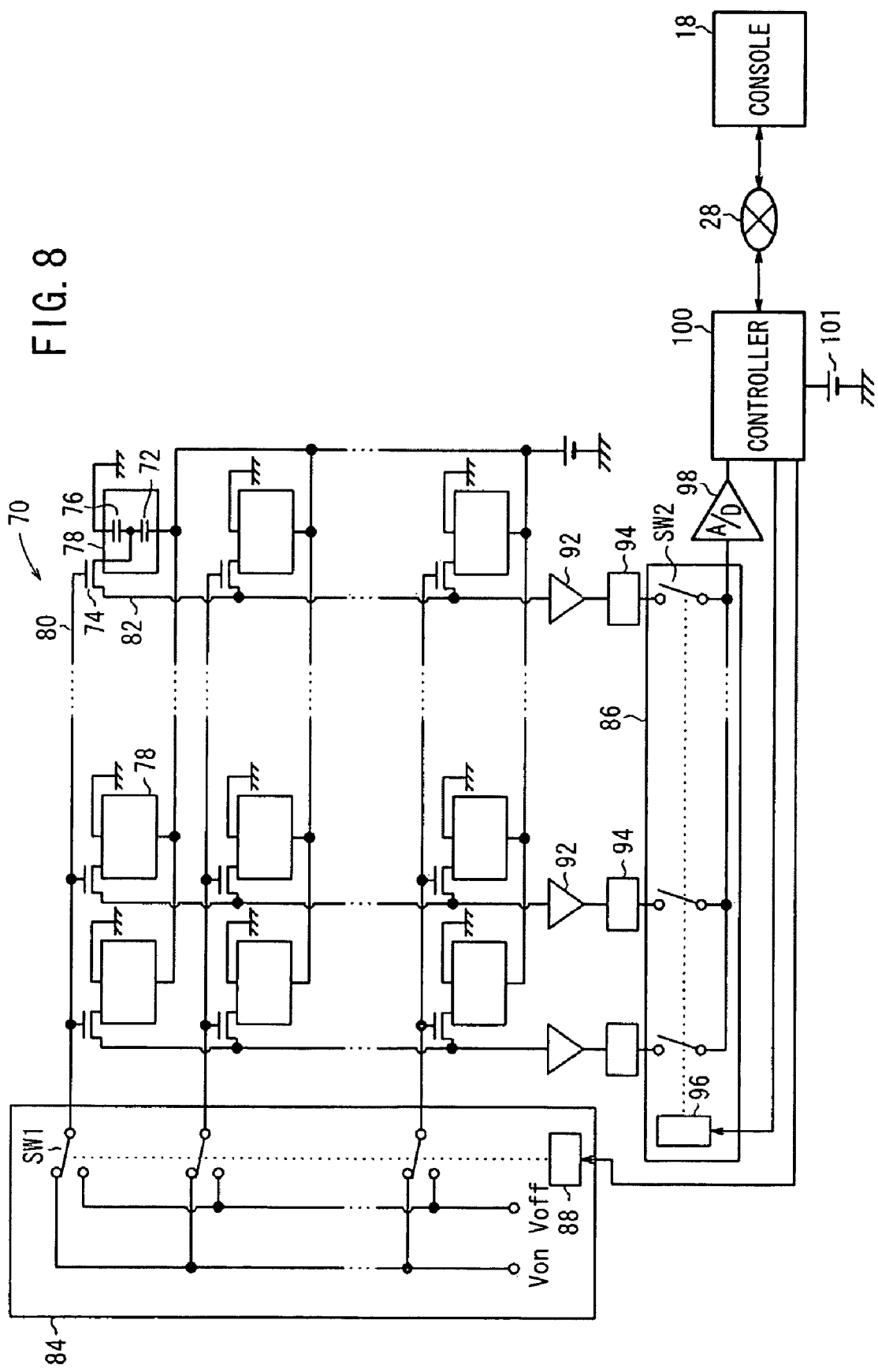
FIG. 8 is a block diagram of a circuit arrangement of a radiation conversion panel that is housed in the first image capturing apparatus.

For example, the first image capturing apparatus 22 may employ a radiation conversion panel 70 having a circuit arrangement shown in FIG. 8, rather than the stimulable phosphor panel P' housed in the casing 222.

As shown in FIG. 8, the radiation conversion panel 70 comprises an array of thin-film transistors (TFTs) 74 arranged in rows and columns, a photoelectric conversion layer 72 made of a material such as amorphous selenium (a-Se) for generating electric charges upon detection of a radiation, the photoelectric conversion layer 72 being disposed on the array of TFTs 74, and an array of storage capacitors 76 connected to the photoelectric conversion layer 72. When the radiation is applied to the radiation conversion panel 70, the photoelectric conversion layer 72 generates electric charges, and the storage capacitors 76 store the generated electric charges. Then, the TFTs 74 are turned on along each row successively to read the electric charges from the storage capacitors 76 as an image signal. In FIG. 8, the photoelectric conversion layer 72 and one of the storage capacitors 76 are shown as a pixel 78, and the pixel 78 is connected to one of the TFTs 74. Details of the other pixels 78 are omitted from illustration. Since amorphous selenium tends to change its structure and lose its function at high temperatures, it needs to be used in a certain temperature range. Therefore, some means for cooling the radiation conversion panel 70 should preferably be provided in the image capturing base 220.

The TFTs 74 connected to the respective pixels 78 are connected to respective gate lines 80 extending parallel to the rows and respective signal lines 82 extending parallel to the columns. The gate lines 80 are connected to a line scanning driver 84, and the signal lines 82 are connected to a multiplexer 86 serving as a reading circuit.

The gate lines 80 are supplied with control signals Von, Voff for turning on and off the TFTs 74 along the rows from the line scanning driver 84. The line scanning driver 84 comprises a plurality of switches SW1 for switching between the gate lines 80 and an address decoder 88 for outputting a selection signal for selecting one of the switches SW1 at a time. The address decoder 88 is supplied with an address signal from a controller 100 which is energized by a battery 101.

The signal lines 82 are supplied with electric charges stored in the storage capacitors 76 of the pixels 78 through the TFTs 74 arranged in the columns. The electric charges supplied to the signal lines 82 are amplified by amplifiers 92 connected respectively to the signal lines 82. The amplifiers 92 are connected through respective sample and hold circuits 94 to the multiplexer 86. The multiplexer 86 comprises a plurality of switches SW2 for successively switching between the signal lines 82, and an address decoder 96 for outputting a selection signal for selecting one of the switches SW2 at a time. The address decoder 96 is supplied with an address signal from the controller 100. The multiplexer 86 is connected to an A/D converter 98. A radiation image information from the multiplexer 86 is converted by the A/D converter 98 into a digital image signal representing radiation image information, which is supplied to the controller 100. The controller 100 supplies the acquired radiation image information through the in-house network 28 to the first console 18 which controls the first image capturing apparatus 22.

The TFTs 74 functioning as switching devices may be combined with other imaging devices such as a CMOS (Complementary Metal-Oxide Semiconductor) image sensor or a CCD (Charge-Coupled Device) image sensor which transfers electric charges while shifting them with shift pulses which correspond to the gate signals for the TFTs.

The radiation conversion panel 70 is a direct-conversion radiation detector which directly converts the dose of the applied radiation X into an electric signal with the photoelectric conversion layer 72. However, the radiation image capturing system 10 may employ an indirect-conversion radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the radiation image capturing system 10 may employ a radiation detector of the light readout type for acquiring radiation image information. The radiation detector of the light readout type operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices to cause the solid-state detecting devices to generate an electric current representing radiation image information. When erasing light is applied to the radiation detector, radiation image information representing a residual electrostatic latent image is erased from the radiation detector, which can thus be reused (see Japanese Laid-Open Patent Publication No. 2000-105297).

Figure 9:
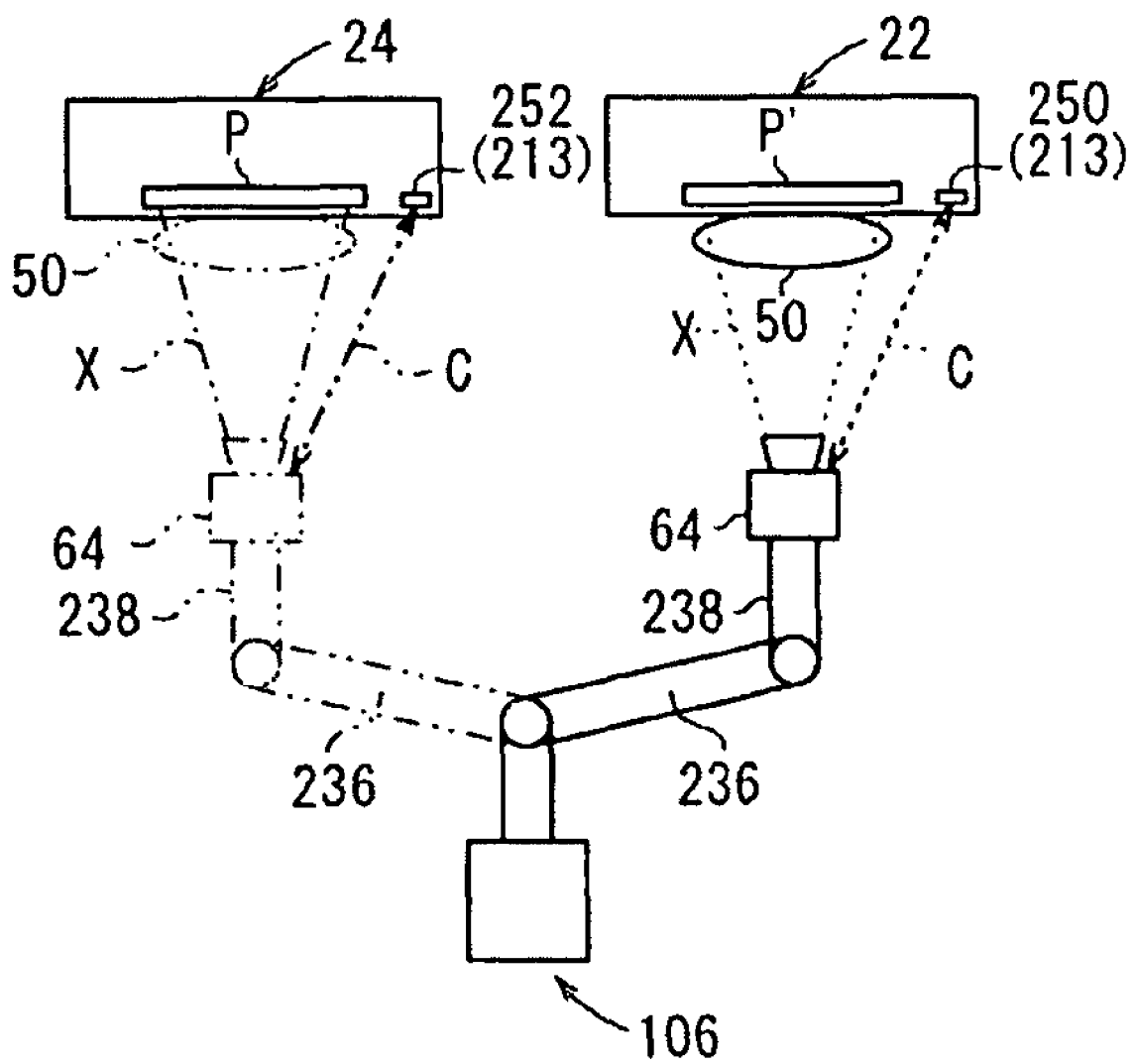
FIG. 9 is a schematic view showing the relationship similar to FIG. 4, but another detecting means is used in place of the detecting means shown in FIG. 4.
Figure 10:
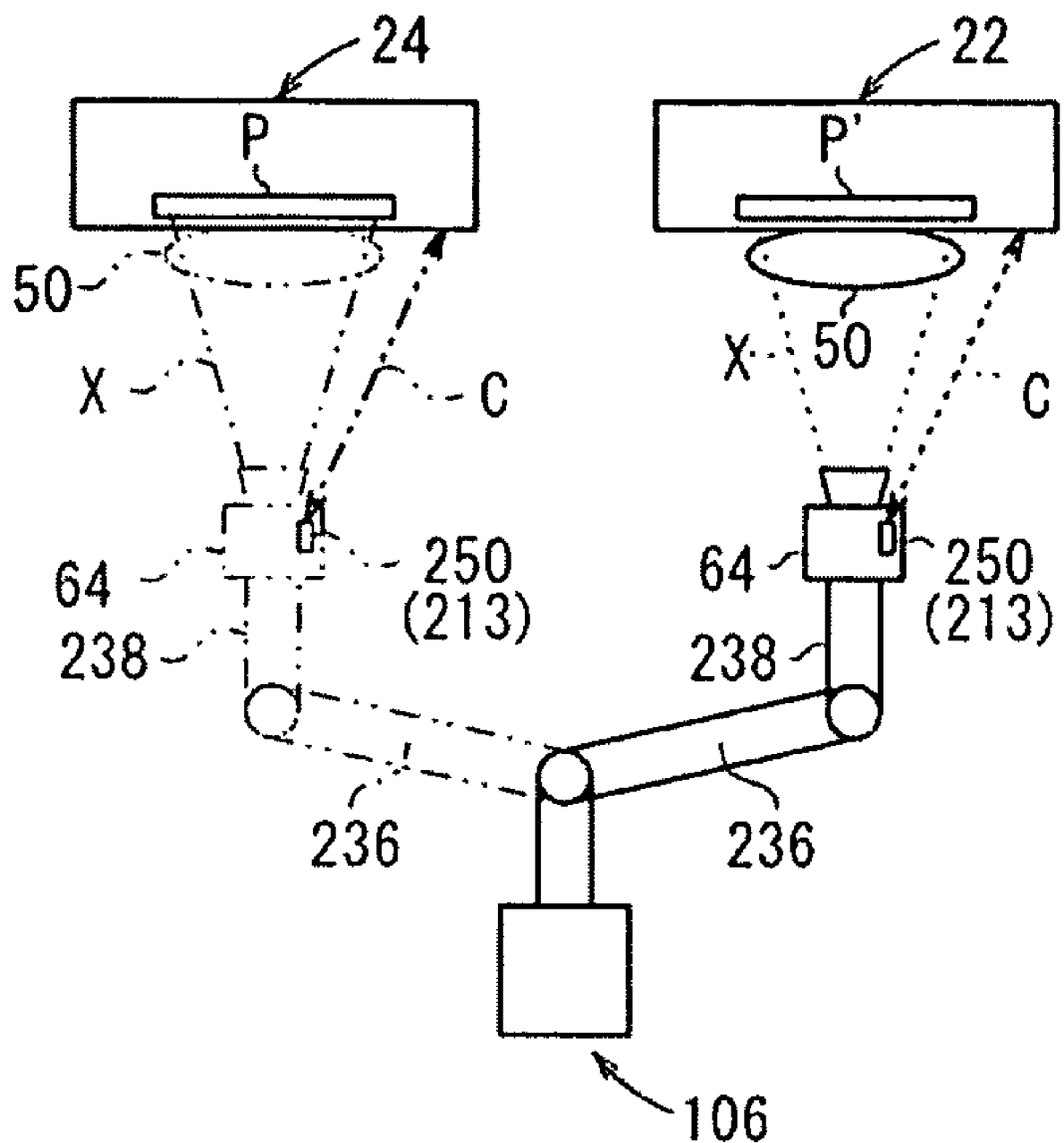
FIG. 10 is a schematic view showing the relationship similar to FIG. 4, but still another detecting means is used in place of the detecting means shown in FIG. 4.
Figure 11:
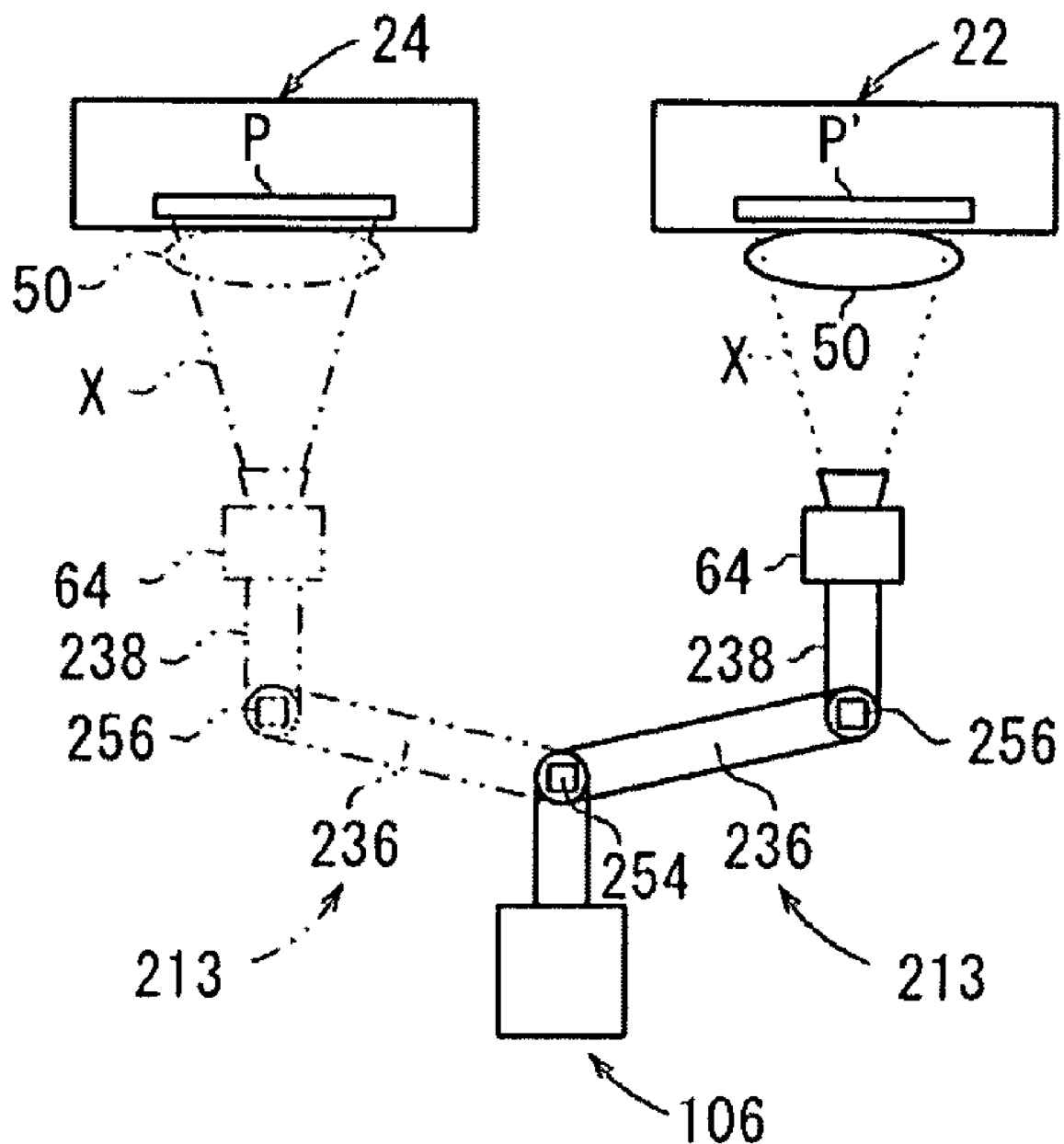
FIG. 11 is a schematic view showing the relationship similar to FIG. 4, but yet another detecting means is used in place of the detecting means shown in FIG. 4.

The detecting means 213 which is made up of the transmitter 200 and the receivers 202, 212 shown in FIGS. 3 and 4 may be replaced with any one of detecting means shown in FIGS. 9 through 11.

FIG. 9 shows a proximity sensor (position detecting sensor) 250 disposed instead of the detecting means 213 in the first image capturing apparatus 22 and a proximity sensor (position detecting sensor) 252 disposed instead of the detecting means 213 in the second image capturing apparatus 24. Each of the proximity sensors 250, 252 sends a signal C (an optical signal, an infrared signal, or an ultrasonic signal) in the direction indicated by the arrow in FIG. 9. When the radiation source 64 is brought into the position facing the first image capturing apparatus 22 or the second image capturing apparatus 24 by the radiological technician who moves the arms 236, 238, the signal C is reflected by the radiation source 64 and detected by the proximity sensor 250 or 252, which supplies a signal indicative of the detection result to the controller 34 via the in-house network 28.

FIG. 10 shows a proximity sensor 250 disposed in the radiation source 64. The proximity sensor 250 sends a signal C in the direction indicated by the arrows in FIG. 10. When the radiation source 64 is brought into the position facing the first image capturing apparatus 22 or the second image capturing apparatus 24 by the radiological technician who moves the arms 236, 238, the signal C is reflected by the first image capturing apparatus 22 or the second image capturing apparatus 24 and detected by the proximity sensor 250, which supplies a signal indicative of the detection result to the controller 34 via the in-house network 28.

FIG. 11 shows potentiometers (angle detecting sensors) 254, 256 disposed on respective shafts of the arms 236, 238. The potentiometers 254, 256 detect angular displacements of the arms 236, 238, and send a signal D representative of the detected angular displacements as the detection result to the controller 34 via the in-house network 28. Since the angular displacements depend on the angle of the radiation source 64 with respect to the first image capturing apparatus 22 or the second image capturing apparatus 24, the controller 34 judges that the radiation source 64 is facing the first image capturing apparatus 22 or the second image capturing apparatus 24 when the angular displacements represented by the signal D correspond to the angle of the radiation source 64 which is facing the first image capturing apparatus 22 or the second image capturing apparatus 24.

The proximity sensors 250, 252 and the potentiometers 254, 256 shown in FIGS. 9 through 11 are also as effective as the detecting means 213 shown in FIG. 4.

In the above embodiment, the doctor sets patient information using the HIS 12, and the doctor or the radiological technician sets image capturing instruction information using the RIS 14. The information is supplied to the host console 16 via the in-house network 28, and then supplied from the host console 16 to the first console 18 or the second console 20. However, the doctor or the radiological technician may set patient information and image capturing instruction information directly on the host console 16, the first console 18, or the second console 20. Alternatively, the doctor or the radiological technician may set patient information and image capturing instruction information using the HIS 12 or the RIS 14.

Although certain preferred embodiments of the present invention have been shown and described in detail, it should be understood that various changes and modifications may be made therein without departing from the scope of the appended claims.

What is claimed is:

1. A radiation image capturing system comprising:
  a plurality of image capturing apparatus for capturing a radiation image of a subject by a radiation emitted from a radiation source and applied through the subject;
  a detecting unit for detecting which of the image capturing apparatus the radiation source is oriented to; and a plurality of processors for setting an image capturing mode for the radiation image based on a detection result from the detecting unit and controlling a process of capturing the radiation image with the image capturing apparatus which is detected by the detecting unit in the set image capturing mode, wherein each of the processors has a plurality of image capturing modes respectively for each of the image capturing apparatus, each of the image capturing modes comprises a mode for capturing the radiation image by applying the radiation from the radiation source through the subject to one of the image capturing apparatus, the processors comprise a host console, a first console, and a second console, the host console selects one of the image capturing modes depending on one of the image capturing apparatus to which the radiation source is oriented, based on the detection result, and controls the one of the image capturing apparatus to which the radiation source is oriented to capture the radiation image, based on the selected one of the image capturing modes, the first console controls a first image capturing apparatus of the image capturing apparatus, and if the detection result indicates that the radiation source is oriented to the first image capturing apparatus, the first console selects one of the image capturing modes depending on the first image capturing apparatus and controls the first image capturing apparatus to capture the radiation image, based on the selected one of the image capturing modes, and the second console controls a second image capturing apparatus of the image capturing apparatus, and if the detection result indicates that the radiation source is oriented to the second image capturing apparatus, the second console selects one the image capturing modes depending on the second image capturing apparatus and controls the second image capturing apparatus to capture the radiation image, based on the selected one of the image capturing modes.

2. A radiation image capturing system according to claim 1, wherein one of the image capturing apparatus comprises an image capturing apparatus which has a radiation conversion panel built-in and another one of the image capturing apparatus comprises an image capturing apparatus which is loadable with the radiation conversion panel from outside thereof;

the image capturing modes include a first mode for capturing the radiation image by applying the radiation from the radiation source through the subject to the one of the image capturing apparatus, and a second mode for capturing the radiation image by applying the radiation from the radiation source through the subject to the other one of the image capturing apparatus; and if the detection result indicates that the radiation source is oriented to the one of the image capturing apparatus or the other one of the image capturing apparatus, the processor selects one of the first mode and the second mode depending on the image capturing apparatus to which the radiation source is oriented, and controls the image capturing apparatus to which the radiation source is oriented to capture the radiation image, based on the selected one of the image capturing modes.

3. A radiation image capturing system according to claim 1, wherein the detecting unit comprises a transmitter disposed on the radiation source and a receiver disposed on the image capturing apparatus; and when the receiver receives a signal sent from the transmitter, the receiver outputs the received signal as the detection result to the processor.

4. A radiation image capturing system according to claim 1, wherein the detecting unit comprises a position detecting sensor disposed on the radiation source or the image capturing apparatus; and when the position detecting sensor detects that the radiation source faces the image capturing apparatus, the position detecting sensor outputs a detected signal as the detection result to the processor.

5. A radiation image capturing system according to claim 1, wherein the detecting unit comprises an angle detecting sensor disposed on the radiation source; and the angle detecting sensor detects an angle of the radiation source with respect to the image capturing apparatus, and outputs a signal indicative of the detected angle as the detection result to the processor.

6. A method of capturing a radiation image of a subject by applying a radiation from a radiation source through the subject to one of a plurality of image capturing apparatus, comprising:

a detecting step for detecting which of the image capturing apparatus the radiation source is oriented to; and a setting and controlling step for setting an image capturing mode for the radiation image based on a detection result from the detecting step, and making one of a plurality of processors control a process of capturing the radiation image with the image capturing apparatus detected in the set image capturing mode, wherein each of the processors has a plurality of image capturing modes respectively for each of the image capturing apparatus, each of the image capturing modes comprises a mode for capturing the radiation image by applying the radiation from the radiation source through the subject to one of the image capturing apparatus, the processors comprise a host console, a first console, and a second console, the host console selects one of the image capturing modes depending on one of the image capturing apparatus to which the radiation source is oriented, based on the detection result, and controls the one of the image capturing apparatus to which the radiation source is oriented to capture the radiation image, based on the selected one of the image capturing modes, the first console controls a first image capturing apparatus of the image capturing apparatus, if the detection result indicates that the radiation source is oriented to the first image capturing apparatus, the first console selects one of the image capturing modes depending on the first image capturing apparatus and controls the first image capturing apparatus to capture the radiation image, based on the selected one of the image capturing modes, and the second console controls a second image capturing apparatus of the image capturing apparatus, if the detection result indicates that the radiation source is oriented to the second image capturing apparatus, the second console selects one of the image capturing modes depending on the second image capturing apparatus and controls the second image capturing apparatus to capture the radiation image, based on the selected one of the image capturing modes.

* * * * *